(12) United States Patent
Kim et al.

(10) Patent No.: US 11,696,387 B2
(45) Date of Patent: Jul. 4, 2023

(54) PLASMA GENERATING DEVICE

(71) Applicant: FEMTO SCIENCE INC, Hwaseong-si (KR)

(72) Inventors: Moo Hwan Kim, Hwaseong-si (KR); Yeon Sook Chang, Hwaseong-si (KR)

(73) Assignee: FEMTO SCIENCE INC, Hwaseong-si (KR)

( * ) Notice: Subject to any disclaimer, the term of this patent is extended or adjusted under 35 U.S.C. 154(b) by 131 days.

(21) Appl. No.: 17/502,770

(22) Filed: Oct. 15, 2021

(65) Prior Publication Data
US 2022/0353981 A1    Nov. 3, 2022

(30) Foreign Application Priority Data
Apr. 29, 2021    (KR) .................. 10-2021-0055635

(51) Int. Cl.
*H05H 1/24*    (2006.01)
*A61N 1/44*    (2006.01)

(52) U.S. Cl.
CPC ........ *H05H 1/24* (2013.01); *A61N 1/44* (2013.01)

(58) Field of Classification Search
None
See application file for complete search history.

(56) References Cited

U.S. PATENT DOCUMENTS

| | | | |
|---|---|---|---|
| D935,022 S * | 11/2021 | Kim | D24/144 |
| 11,229,806 B2 * | 1/2022 | Barbarat | H05H 1/2406 |
| 11,508,559 B2 * | 11/2022 | Kim | H05H 1/34 |
| 2011/0061685 A1 * | 3/2011 | Sommers | C23C 16/4407 |
| | | | 134/26 |
| 2013/0167885 A1 * | 7/2013 | Sommers | H01L 21/67724 |
| | | | 134/115 R |
| 2019/0365215 A1 * | 12/2019 | Sagiv | H05H 1/2406 |
| 2020/0077503 A1 * | 3/2020 | Pichler | H10N 30/40 |
| 2020/0083023 A1 * | 3/2020 | Kim | A61N 1/44 |
| 2020/0362505 A1 * | 11/2020 | Razouki | D06F 43/085 |
| 2021/0196969 A1 * | 7/2021 | Yeates | A61L 2/0011 |
| 2021/0225620 A1 * | 7/2021 | Kim | H01J 37/32449 |
| 2021/0260394 A1 * | 8/2021 | Wunderl | A61L 2/0011 |
| 2022/0353981 A1 * | 11/2022 | Kim | H05H 1/24 |
| 2022/0406564 A1 * | 12/2022 | Kim | H01J 37/3211 |
| 2023/0005662 A1 * | 1/2023 | Kim | H01F 5/02 |

FOREIGN PATENT DOCUMENTS

KR    20-2011-0003121 U    3/2011

* cited by examiner

*Primary Examiner* — Srinivas Sathiraju
(74) *Attorney, Agent, or Firm* — Paratus Law Group, PLLC

(57) ABSTRACT

A plasma generating device includes: a supply module for supplying gas; a handset for generating plasma from the supplied gas; and a control module attachable to or detachable from the supply module, wherein the plasma generating device switches to a button control mode or a dial control mode depending on the manner in which the handset is connected to the control module and the supply module.

20 Claims, 9 Drawing Sheets

PLASMA GENERATING DEVICE

CROSS-REFERENCE TO RELATED APPLICATION

The present application claims priority to Korean Patent Application No. 10-2021-0055635, filed on Apr. 29, 2021, which is hereby incorporated by reference in its entirety.

BACKGROUND

The present disclosure relates to a plasma generating device that has a control module for controlling the flow of plasma gas and a supply module for supplying plasma gas, the control module and the supply module being made attachable and detachable.

Plasma is a collection of particles consisting of ion nuclei and free electrons which is generated when a temperature of a material in a gas state is raised by continuously applying heat to it. It is called the "fourth state of matter" in addition to the three forms of matter: solid, liquid, and gas.

Recent studies reveal that plasma energy has been remarkably effective for skin regeneration. Plasma for skin regeneration delivers energy only to the tissues in the skin to be treated without direct contact with the skin, and therefore it does not cause any damage to the epidermis which acts as a protective layer until the skin is regenerated.

Moreover, its skin regeneration effects are not temporary but rather sustained, and the skin will keep improving over time.

Plasma helps to dramatically reduce facial lines and wrinkles, tighten skin, brighten skin tone, and improve skin texture and pigmentation, making it a great treatment for improving overall skin health and appearance. Other advantages are that it involves no pain during treatment and treats even curved areas such as around the mouth or eyes and on the cheekbones. Besides, plasma is known for being highly effective in healing wounds.

Korean Utility Model Laid Open No. 20-2011-0003121 concerns a handheld beauty device using plasma, which includes an insulator 10 that is hollow inside, a gas injection tube 20 disposed on one side of the insulator 10 to supply gas, a first electrode 30 with a hollow disposed on the other side of the insulator 10, that penetrates the insulator 10 to communicate with the gas injection tube 20 and receive electric current, a second electrode 40 disposed on the other side of the insulator 10, that holds the first electrode 30 inside, has a spray hole at a position corresponding to a front end of the first electrode 30, and is grounded to generate plasma by interacting with the first electrode 30, a battery 50 for supplying electric current to the first electrode 30, and a controller 60 for controlling the electric current supplied to the first electrode 30.

SUMMARY

However, the above conventional technology is problematic in that it requires a general gas bombe which supplies gas to generate plasma, and in that this general gas bombe is hard to carry due to its large size and has limitations in space.

In view of this, the present disclosure is directed to provide a plasma generating device with enhanced portability that comes with a compact-sized, easy-to-carry gas bombe and a control module and a supply module that can be separated or combined depending on where the plasma generating device is installed and how it is used.

The present disclosure provides a plasma generating device including: a supply module for supplying gas; a handset for generating plasma from the supplied gas; and a control module attachable to or detachable from the supply module, wherein the plasma generating device may switch to a button control mode or a dial control mode depending on the manner in which the handset is connected to the control module and the supply module.

Furthermore, in the button control mode, the gas may be supplied from the supply module to the control module, the supplied gas may be provided from the control module to the handset, and the control module may control the flow of gas supplied to the handset.

Furthermore, in the dial control mode, while the supply module and the control module are being separated, the gas may be provided from the supply module to the handset, and the supply module may control the flow of gas supplied to the handset.

Furthermore, the supply module may include a gas bombe and a mounting guide member.

Furthermore, the supply module may include a gas bombe mounting portion where the gas bombe and the mounting guide portion are mounted.

Furthermore, the gas bombe mounting portion may correspond in shape to the mounting guide member.

Furthermore, the mounting guide member may be coupled to a gas bombe exit and mounted on the gas bombe mounting portion.

Furthermore, the mounting guide member may include a pressure regulating member.

Furthermore, the mounting guide member may include a display member for visually showing the pressure of gas emitted from the gas bombe.

Furthermore, the handset may be connected to the control module by a first connecting pipe.

Furthermore, the control module may be connected to the supply module by a second connecting pipe.

Furthermore, the control module may have a handset mounting portion where the handset is mounted.

Furthermore, the control module may control the intensity and duration of plasma generated by the handset.

Furthermore, a recessed portion may be formed on one side of the control module, and a protruding portion may be formed on one side of the supply module, wherein the protruding portion may be inserted into the recessed portion such that the supply module and the control module are attached together.

Furthermore, the protruding portion or the recessed portion may include a magnetic material such that the control module and the supply module are attached together by magnetic force.

Furthermore, a top side of the control module and a top side of the supply module may be sloped.

Furthermore, the angle of slope on the top side of the control module may coincide with the angle of slope on the top side of the supply module.

Furthermore, the gas bombe mounting portion may be sloped, a top side of the supply module may be sloped, and the angle of slope on the gas bombe mounting portion may coincide with the angle of slope on the top side of the supply module.

Furthermore, the handset mounting portion may be sloped, a top side of the control module may be sloped, and the angle of slope on the handset mounting portion may coincide with the angle of slope on the top side of the control module.

DETAILED DESCRIPTION

Figure 1:
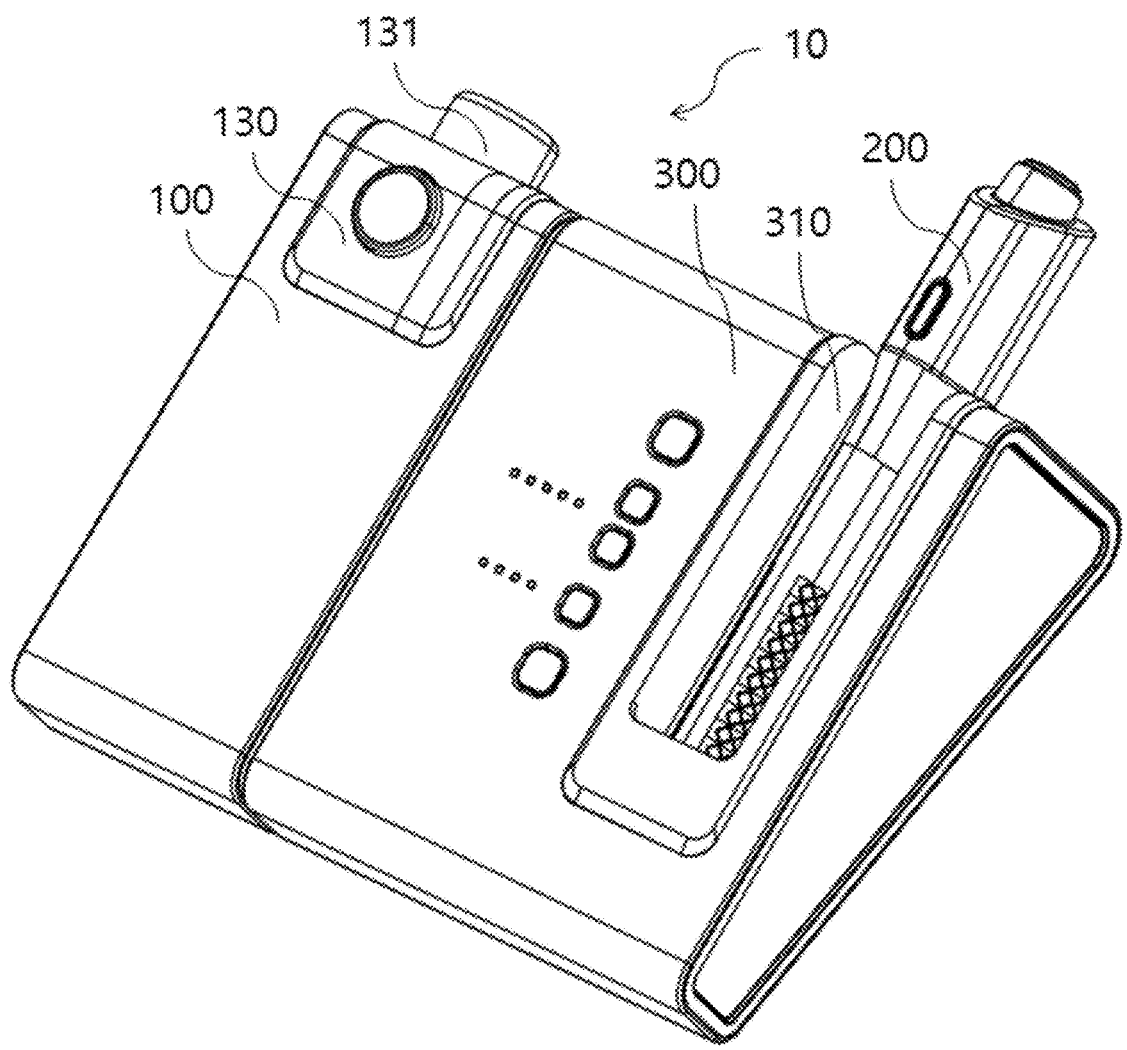
FIG. 1 is a perspective view of a configuration of a plasma generating device according to the present disclosure.

As the disclosure allows for various changes and numerous embodiments, particular embodiments will be illustrated in the drawings and described in detail. However, it should be understood that the present disclosure is not limited to particular modes of practice, but encompasses all changes, equivalents, and substitutes included in the technical spirit and technical scope to be described below.

Figure 2:
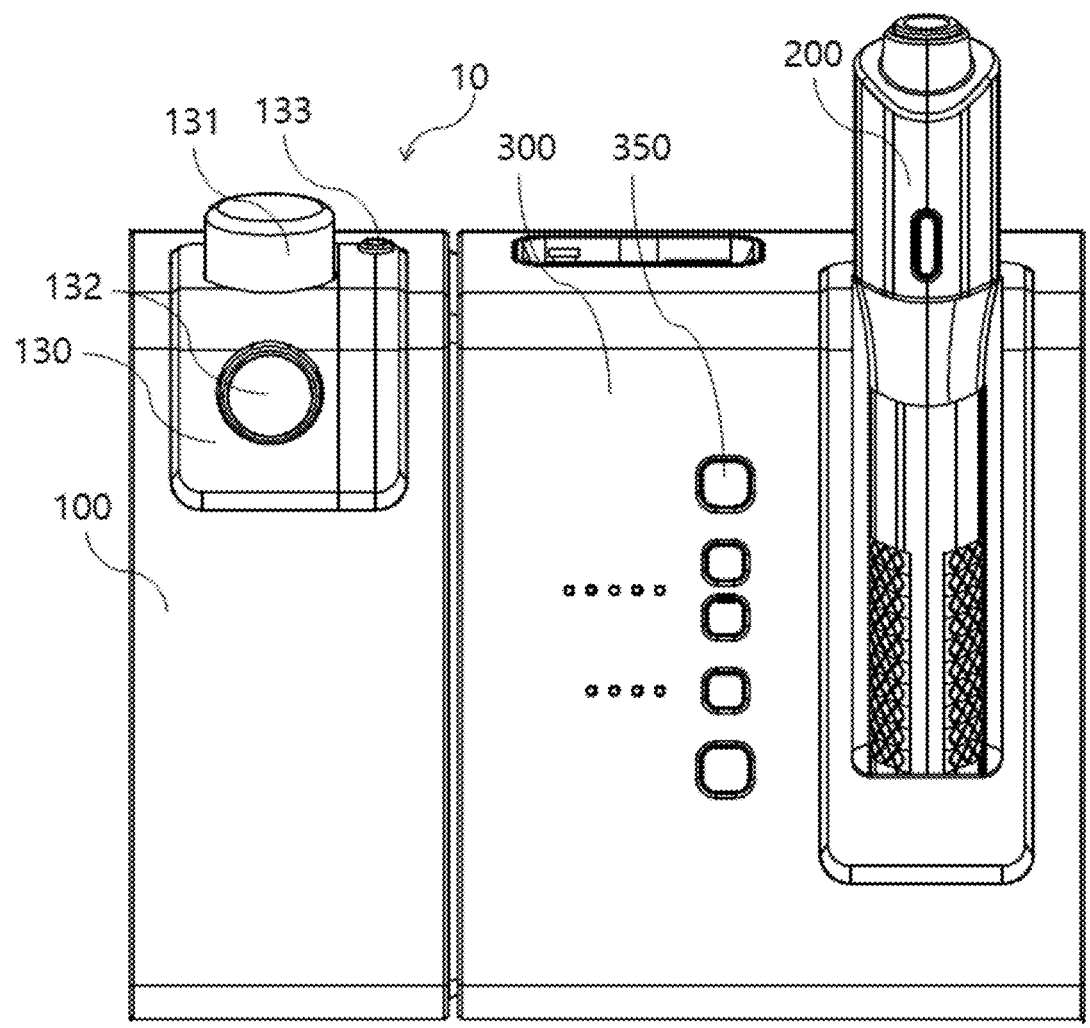
FIG. 2 is a plan view of the configuration of the plasma generating device according to the present disclosure.
Figure 3:
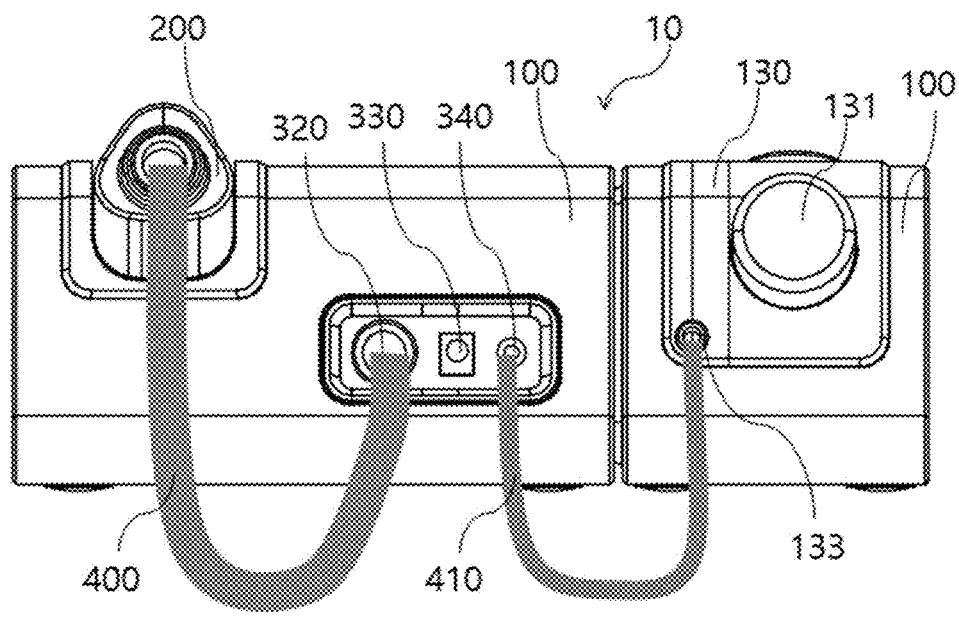
FIG. 3 is a rear view of the configuration of the plasma generating device according to the present disclosure.

FIGS. 1 to 3 schematically depict a configuration of a plasma generating device 10 according to an embodiment of the present disclosure. Referring to FIGS. 1 to 3, the plasma generating device 10 may include a supply module 100, a handset 200, and a control module 300.

The plasma generating device 10 according to the present disclosure is a device in which the supply module 100 including a small, compact-sized gas bombe 120 and the control module 300 for controlling plasma emitted from the handset 200 are integrated as a single unit, making the device easy to carry. The device offers better convenience of use because the gas bombe 120 can be used on an ongoing basis by replacing its single-use cartridge. Also, the plasma generating device 10 may be placed and used on a moving or stationary table at a hospital, home, etc., and made smaller in height compared to its breadth or width to ensure structural safety so as not to collapse while the table is being moved, thus lowering its center of gravity, and its top side may be sloped so that the user can easily and visually see buttons on the top side.

Figure 6:
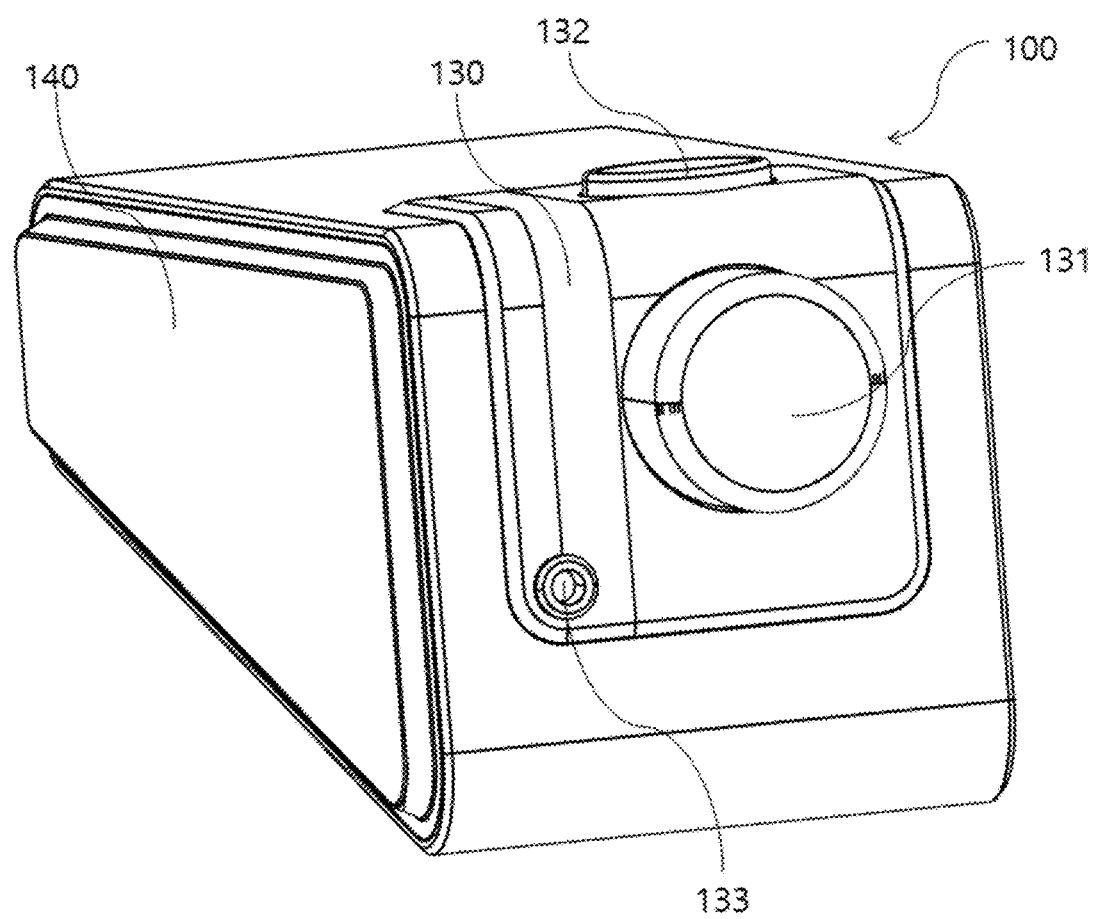
FIG. 6 is a perspective view of a supply module of the plasma generating device according to the present disclosure.
Figure 7:
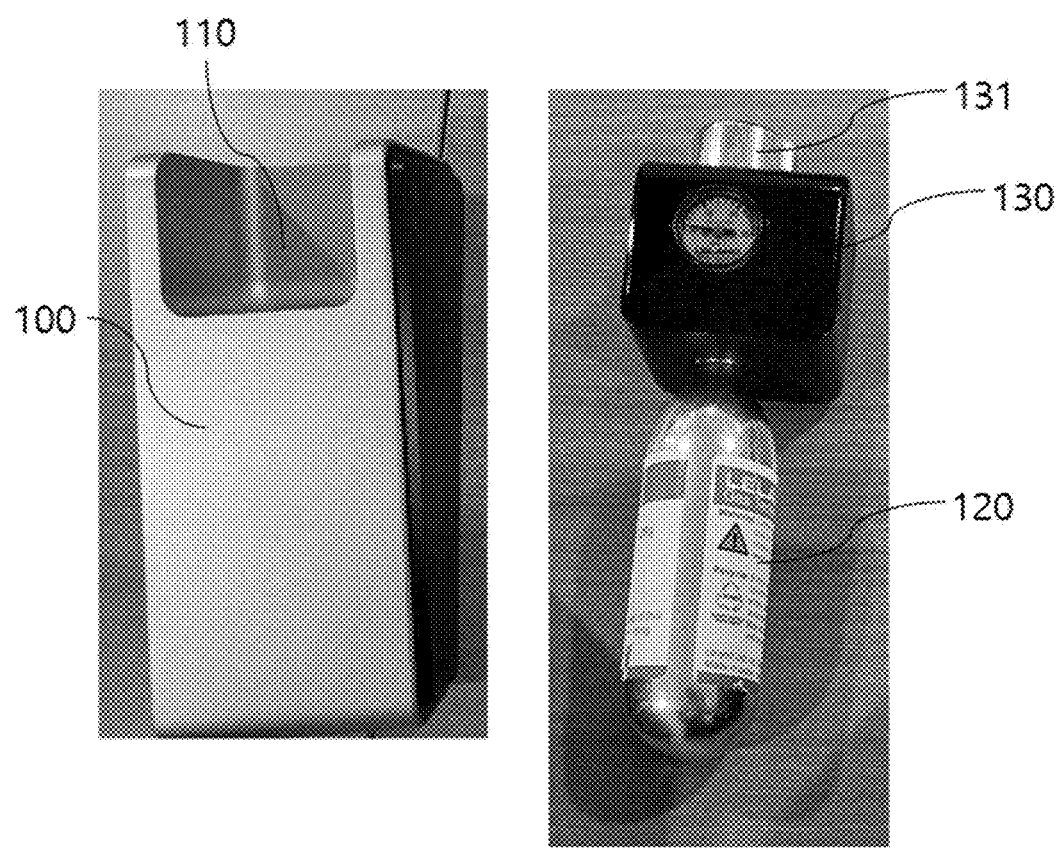
FIG. 7 shows a gas bombe before it is mounted on the supply module of the plasma generating device according to the present disclosure.

Referring to FIGS. 6 and 7, the supply module 100 may be a module for supplying gas to generate plasma. The supply module 100 may include the gas bombe 120, a mounting guide member 130 coupled to a gas exhaust of the gas bombe 120, a gas bombe mounting portion 110 for mounting the gas bombe 120, and a protruding portion 140 on one side that is attached to the control module 300.

One side of the supply module 100 is attachable to or detachable from one side of the control module 300, and may be attached to or separated from the control module 300 as required.

The gas bombe 120 may be made compact in size for better portability, and the gas bombe 120 may internally contain, for example, one or more of the following: inert gases used for plasma, such as helium (He), neon (Ne), argon (Ar), krypton (Kr), and xenon (Xe), oxygen ($O_2$), nitrogen ($N_2$), and air.

The mounting guide member 130 is a member that guides the gas bombe 120 to be mounted on the gas bombe mounting portion 110, and may correspond in shape to the gas bombe mounting portion 110. Also, the mounting guide member 130 may include a pressure regulating member 131 coupled to the gas bombe 120, for regulating the discharge pressure of plasma gas emitted from the gas bombe 120, and a display member.

The mounting guide member 130 may be coupled to the gas exhaust of the gas bombe 120 to close a hole of the gas exhaust by a valve and adjust the opening and closing degree of the valve by manipulating the pressure regulating member 131. This way, the flow and pressure of gas emitted from the gas bombe 120 may be regulated. The pressure regulating member 131 may be manipulated such that the pressure of emitted gas is kept between 0.05 bar and 0.3 bar.

Since the mounting guide member 130 corresponds in shape to the gas bombe mounting portion 110, the gas bombe 120 coupled to the mounting guide member 130 may be slidably mounted on the gas bombe mounting portion 110.

A display device 132 may be a device for visually displaying the pressure of gas emitted from the gas bombe 120.

A first connector 133 may be formed on the mounting guide member 130. The first connector 133 is a portion where plasma gas emitted from the gas bombe 120 passes through the inside of the mounting guide member 130 and is released by manipulating the pressure regulating member 131. The first connector 133 may be connected to the control module 300 by a second connecting pipe 410 or to the third handset 200 by a third connecting pipe 420.

In a case where the first connector 133 is connected to a third connector 340 of the control module 300 by the second connecting pipe 410, plasma gas coming out of the first connector 133 may pass through the second connecting pipe 410 and enter the control module 300 via the third connector 340.

In a case where the first connector 133 is connected to a gas intake portion 210 of the handset 200 by the third connecting pipe 420, plasma gas coming out of the first connector 133 may pass through the third connecting pipe 420 and directly enter the handset 200 via the gas intake portion 210. In this case, the flow of plasma gas entering the handset 200 may be controlled by manipulating the pressure regulating member 131 with a hand. The pressure regulating member 131 may include a dial-type rotating handle which allows for flow regulation and precise control by rotating the pressure regulating member 131 while gripping it.

The handset 200 may be an instrument for generating plasma from gas that enters the inside after emitted from the gas bombe 120, by using an internal high-voltage generator. The handset 200 may be made compact in size, making it easy to grip with one hand when using it, and may internally include a battery.

A plasma emitting portion 220 may be formed on one end of the handset 200, and the gas intake portion 210 may be formed on the other hand. The gas intake portion 210 may be connected to the control module 300 via a first connecting pipe 400 or connected to the supply module via the third connecting pipe 420 and receive gas.

Figure 4:
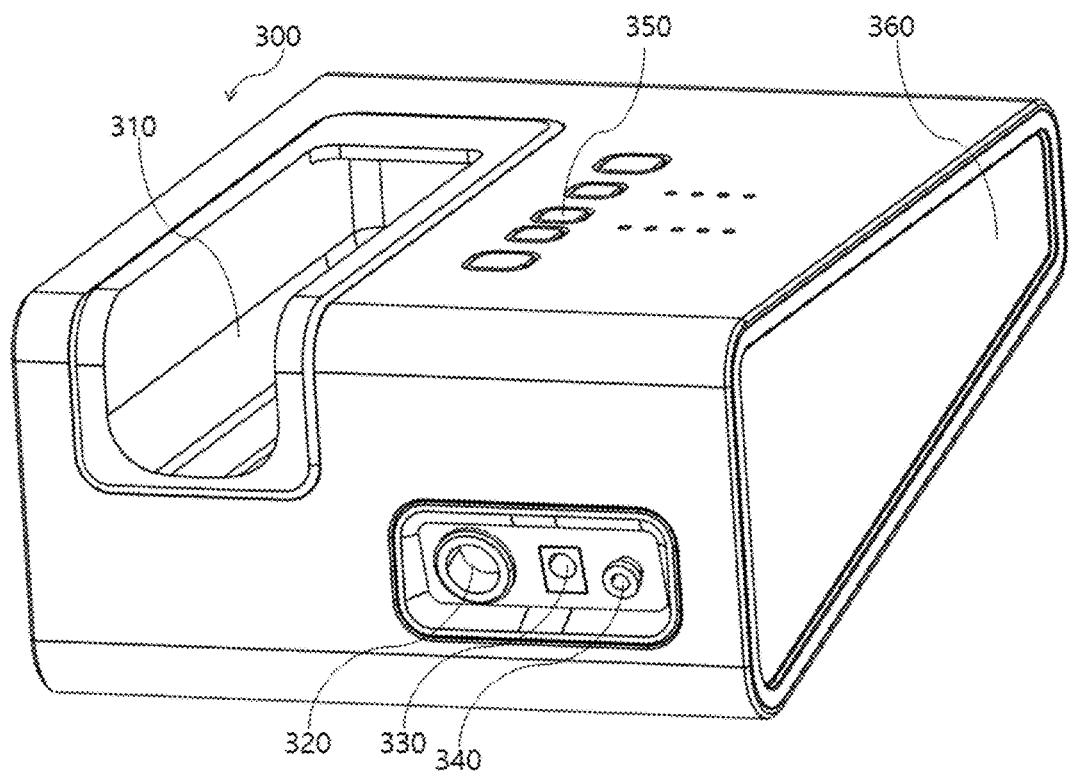
FIG. 4 shows a control module of the plasma generating device according to the present disclosure.
Figure 5:
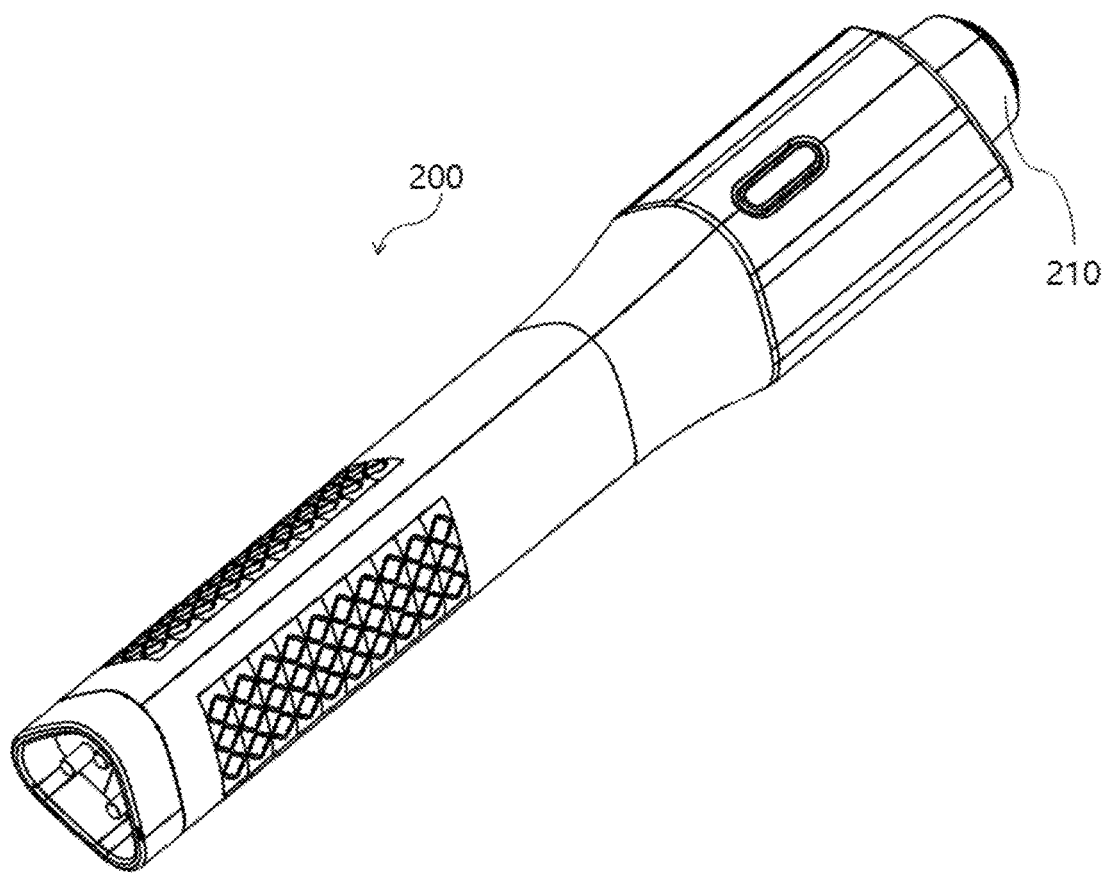
FIG. 5 shows a handset of the plasma generating device according to the present disclosure.

Referring to FIG. 4, the control module 300 may be a portion for controlling the on/off, intensity, duration, etc. of plasma generation of the handset 200. The control module 300 may have a handset mounting portion 310, a handset connector 320, a power connector 330, a supply module connector 340, a control button portion 350, and a recessed portion 360.

The power connector 330 on the control module 300 may receive power from an external power source via an adapter.

The handset connector 320 may be connected to the gas intake portion of the handset 200 via the first connecting pipe 400 so that plasma gas passed through the control module 300 enters the handset 200.

The handset connector 320 may be connected to the handset 200 via the first connecting pipe 400 and connected to the supply module 100 via the second connecting pipe 410.

The control module 300 may have the handset mounting portion 310 where the handset 200 is mounted, and the handset 200 may be slidably mounted and fixed to the handset mounting portion 310.

A top side of the control module 300 and a top side of the supply module 100 may be sloped. The angle of slope on the top side of the control module 300 may coincide with the angle of slope on the top side of the supply module 100.

The gas bombe mounting portion 110 may be sloped, and the angle of slope on the gas bombe mounting portion 110 may coincide with the angle of slope on the top side of the supply module 100. The slope on the gas bombe mounting portion 110 lowers the center of gravity compared to when the gas bombe 120 is placed lengthwise perpendicular to the ground, making it more structurally stable.

The handset mounting portion 310 may be sloped, and the angle of slope on the handset mounting portion 310 may coincide with the angle of slope on the top side of the control module 300. The slope on the handset mounting portion 310 lowers the center of gravity compared to when the handset 200 is placed lengthwise perpendicular to the ground, making it more structurally stable.

The protruding portion 140 may be formed on one side of the supply module 100, and the recessed portion 360 may be formed on one side of the control module 300. Since the recessed portion 360 on the control module 300 corresponds in shape to the protruding portion 140, the protruding portion 140 may be inserted into the recessed portion 360 such that the supply module 100 and the control module 300 may be attached together.

The protruding portion 140 and/or the recessed portion 360 may include a magnetic material, and, when the protruding portion 140 is inserted into the recessed portion 360, the protruding portion 140 and the recessed portion 360 may be attached together by magnetic force. For example, the magnetic material may be a magnet.

An attachment/detachment surface of the supply module 100 and an attachment/detachable surface of the control module 300 may be identical in shape and width, and the supply module 100 and the control module 300 may be identical in height.

Figure 8:
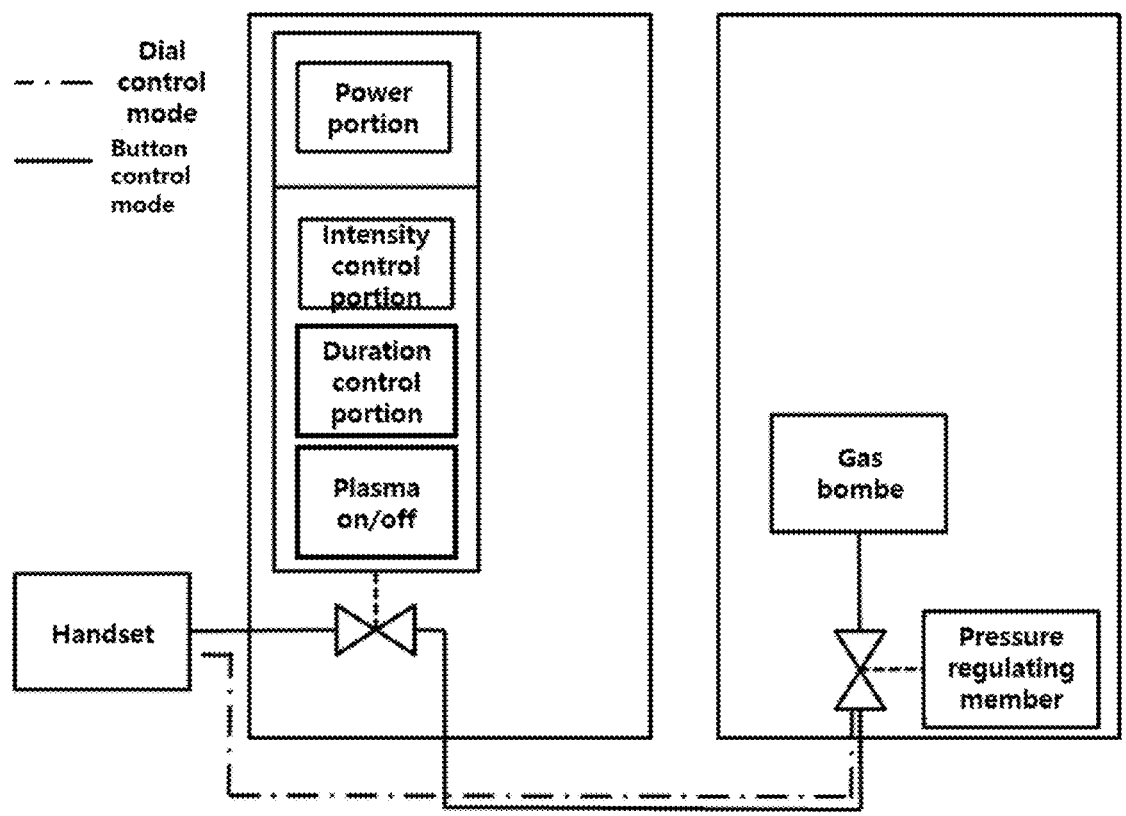
FIG. 8 shows the flow of plasma gas depending on the mode of the plasma generating device according to the present disclosure.

Referring to FIG. 8, the plasma generating device 10 according to the present disclosure may switch to a button control mode or a dial control mode as the handset 200 is connected to the control module 300 and the supply module 100 in a different manner depending on whether the supply module 300 and the supply module 100 are attached to or separated from each other.

In one embodiment, the button control mode may refer to a mode in which plasma from the handset 200 is controlled while the supply module 300 and the control module 100 are attached together as a single unit. In the button control mode, the supply module 300 may be connected to the control module 300 via the second connecting pipe 410 to supply plasma gas to the control module 300, and the control module 300 may be connected to the handset 200 via the first connecting pipe 400 to supply plasma gas from the supply module 200 to the handset 200. In this case, the intensity, duration, on/off, etc. of plasma jets emitted from the handset may be regulated through the control button portion 350 on the control module 300.

In another embodiment, the dial control mode is a mode in which plasma is generated using power from the battery included in the handset 200 by separating the supply module 300 and the control module 200 and connecting the supply module 300 directly to the handset 200 via the third connecting pipe 420. In this mode, the control module 100 is excluded, which may lead to a reduction in the volume of the device and further improve the device's portability. In this case, the intensity of plasma generated by the handset 200 may be regulated by regulating the flow of plasma gas emitted from the gas bombe 120 by manipulating the pressure regulating member 131. The third connecting pipe 420 may connect the first connector 133 of the supply module 100 and the gas intake portion 210 of the handset 200.

Figure 9:
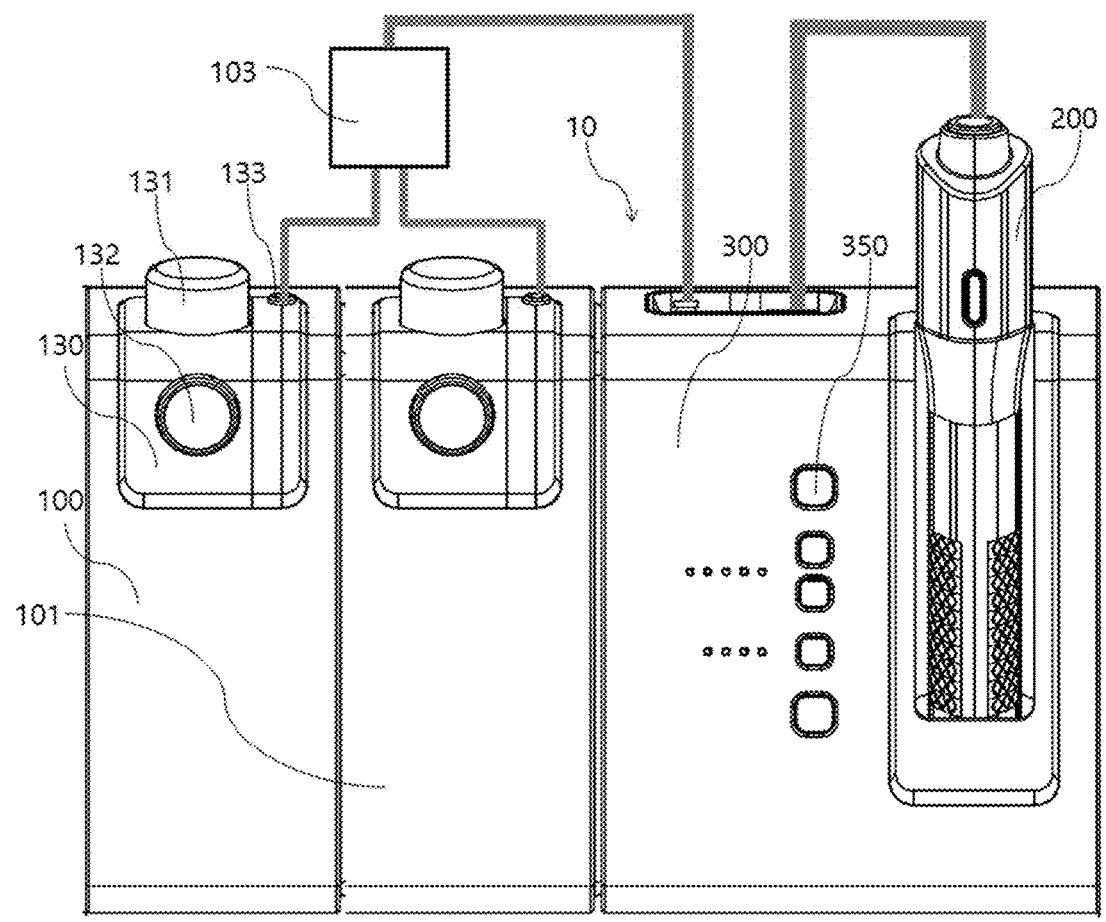
FIGS. 9 and 10 show a plurality of supply modules included in the plasma generating device according to the present disclosure.
Figure 10:
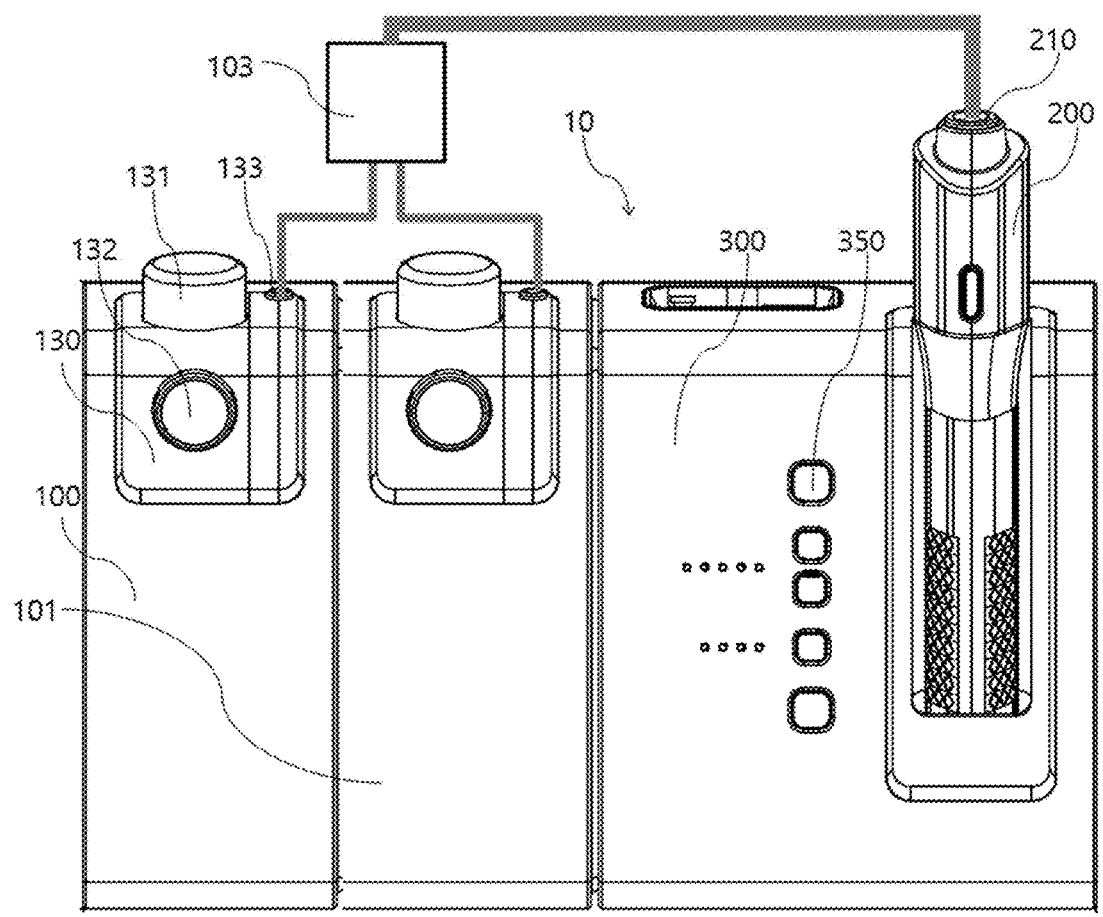

Referring to FIGS. 9 and 10, in the plasma generating device in the present disclosure, a plurality of supply modules that supply different types of gases may be attached or detached, and gases supplied from the respective supply modules 100 and 101 may be introduced into a mixer 103 and mixed there at a predetermined ratio. The gases mixed in the gas mixer 103 may be supplied to the third connector 340 of the control module 300 in the button control mode, or may be supplied to the gas intake portion 210 of the handset 200 in the dial control mode.

The gas mixer 103 may have a pressure display portion to visually show the pressure of the gas mixture and regulate the pressure and mixing ratio of the gas mixture by manipulating the pressure regulating members 131 of the respective supply modules 100 and 101.

The plurality of supply modules are attachable to or detachable from each other. The protruding portion 140 may be formed on one side of one supply module 100, and the protruding portion 140 may include a magnetic material, so that the other side of the other supply module and the protruding portion 140 may be attached together by magnetic force. In this way, the plurality of supply modules may be aligned in a row and successively attached.

While the present technology has been described in the foregoing with reference to an embodiment, the technology is by no means limited to the embodiment. The embodiment may be modified and altered without departing from the gist and scope of the technology, and those skilled in the art will appreciate that such modifications and alterations fall within the scope of the present technology.

The plasma generating device according to the present disclosure may be used in various modes since the supply module and the control module can be attached or detached depending on where the plasma generating device is installed and how it is used.

Moreover, the plasma generating device may be placed and used on a moving table or the like because its center of gravity is low due to its structure, and the device may be held in a stable position even when the table is being moved.

What is claimed is:
1. A plasma generating device comprising:
a supply module for supplying gas;

a handset for generating plasma from the supplied gas; and a control module for controlling the flow of gas supplied to the handset, wherein the supply module is attachable to or detachable from the control module.

2. The plasma generating device of claim 1, wherein an attachment/detachment surface of the supply module and an attachment/detachment surface of the control module are identical in shape.

3. The plasma generating device of claim 2, wherein the supply module and the control module are identical in height.

4. The plasma generating device of claim 1, wherein the supply module comprises a gas bombe, a mounting guide member, and a gas bombe mounting portion, wherein the mounting guide member is coupled to a gas bombe exhaust and mounted on the gas bombe mounting portion.

5. The plasma generating device of claim 4, wherein the mounting guide member comprises a pressure regulating member.

6. The plasma generating device of claim 4, wherein the mounting guide member comprises a display member for visually showing the pressure of gas emitted from the gas bombe.

7. The plasma generating device of claim 4, wherein the gas bombe mounting portion is sloped, a top side of the supply module is sloped, and the angle of slope on the gas bombe mounting portion coincides with the angle of slope on the top side of the supply module.

8. The plasma generating device of claim 1, wherein the handset is connected to the control module by a first connecting pipe.

9. The plasma generating device of claim 1, wherein the control module is connected to the supply module by a second connecting pipe.

10. The plasma generating device of claim 1, wherein the control module has a handset mounting portion where the handset is mounted.

11. The plasma generating device of claim 10, wherein the handset mounting portion is sloped, a top side of the control module is sloped, and the angle of slope on the handset mounting portion coincides with the angle of slope on the top side of the control module.

12. The plasma generating device of claim 1, wherein the control module controls the intensity and duration of plasma generated by the handset.

13. The plasma generating device of claim 1, wherein a recessed portion is formed on one side of the control module, and a protruding portion is formed on one side of the supply module, wherein the protruding portion is inserted into the recessed portion such that the supply module and the control module are attached together.

14. The plasma generating device of claim 13, wherein the protruding portion or the recessed portion comprises a magnetic material such that the control module and the supply module are attached together by magnetic force.

15. The plasma generating device of claim 1, wherein a top side of the control module and a top side of the supply module are sloped.

16. The plasma generating device of claim 15, wherein the angle of slope on the top side of the control module coincides with the angle of slope on the top side of the supply module.

17. The plasma generating device of claim 1, wherein the plasma generating device switches to a button control mode or a dial control mode depending on the manner in which the handset is connected to the control module and the supply module.

18. The plasma generating device of claim 17, wherein, in the button control mode, the gas is supplied from the supply module to the control module, the supplied gas is provided from the control module to the handset, and the control module controls the flow of gas supplied to the handset.

19. The plasma generating device of claim 17, wherein, in the dial control mode, while the supply module and the control module are being separated, the gas is provided from the supply module to the handset, and the supply module controls the flow of gas supplied to the handset.

20. The plasma generating device of claim 1, further comprising another supply module and a gas mixer, wherein the plurality of supply modules are attachable to or detachable from each other, and the gas mixer is connected to the plurality of supply modules and mixes gases introduced from the plurality of supply modules at a predetermined ratio to supply the gases.

* * * * *